United States Patent [19]

De Jonckheere

[11] Patent Number: 4,917,696
[45] Date of Patent: Apr. 17, 1990

[54] DISPOSABLE DIAPER PANTIE

[75] Inventor: Raphael De Jonckheere, Bondues, France

[73] Assignee: Peaudouce, Societe Anonyme, Linselles, France

[21] Appl. No.: 225,563

[22] Filed: Jul. 28, 1988

Related U.S. Application Data

[60] Continuation of Ser. No. 910,083, Sep. 22, 1986, abandoned, which is a division of Ser. No. 572,071, Jan. 19, 1984, Pat. No. 4,666,542.

[30] Foreign Application Priority Data

Jan. 19, 1983 [FR] France ................................. 83 00780

[51] Int. Cl.⁴ ............................................. A61F 13/16
[52] U.S. Cl. ............................................. 604/385.2
[58] Field of Search ........................... 604/385.2, 358; 156/160, 161, 165

[56] References Cited

U.S. PATENT DOCUMENTS

| | | | |
|---|---|---|---|
| 3,860,003 | 1/1975 | Buell | 604/385.1 |
| 4,300,562 | 11/1981 | Pieniak | 604/373 |
| 4,333,782 | 6/1982 | Pieniak | 604/385.2 |
| 4,352,355 | 10/1982 | Mesek et al. | 604/385.2 |
| 4,407,284 | 10/1983 | Pieniak | 604/385.2 |
| 4,430,086 | 2/1984 | Repke | 604/385.2 |
| 4,437,860 | 3/1984 | Sigl et al. | 604/385.2 |
| 4,515,595 | 5/1985 | Kievit et al. | 604/385.2 |
| 4,573,991 | 3/1986 | Pieniak et al. | 604/385.2 |
| 4,636,207 | 1/1987 | Buell | 604/385.2 |
| 4,640,859 | 2/1987 | Hansen et al. | 604/385.2 |
| 4,666,542 | 5/1987 | De Jonckheere | |

*Primary Examiner*—John D. Yasko
*Assistant Examiner*—Sharon Rose
*Attorney, Agent, or Firm*—Owen, Wickersham & Erickson

[57] ABSTRACT

The starting material consists of a multistrand elastic tape (7) which is fed by the apparatus (11) and then separated by the successive separators (20, 24, 30, 31, 32, 33) into two arrays (35, 36) of four individual elastic strands. Each individual strand passes into a longitudinal groove of an adhesive application unit (37, 38), the strands passing out completely coated with hot melt liquid adhesive at high temperature. Adhesive bonding to the flexible sheet (1) moving in the direction of the arrows (2) is effected as soon as contact is made with the said sheet.

A diaper pantie is obtained which on each side of the absorbent pad has a plurality of elastic strands disposed side by side.

3 Claims, 5 Drawing Sheets

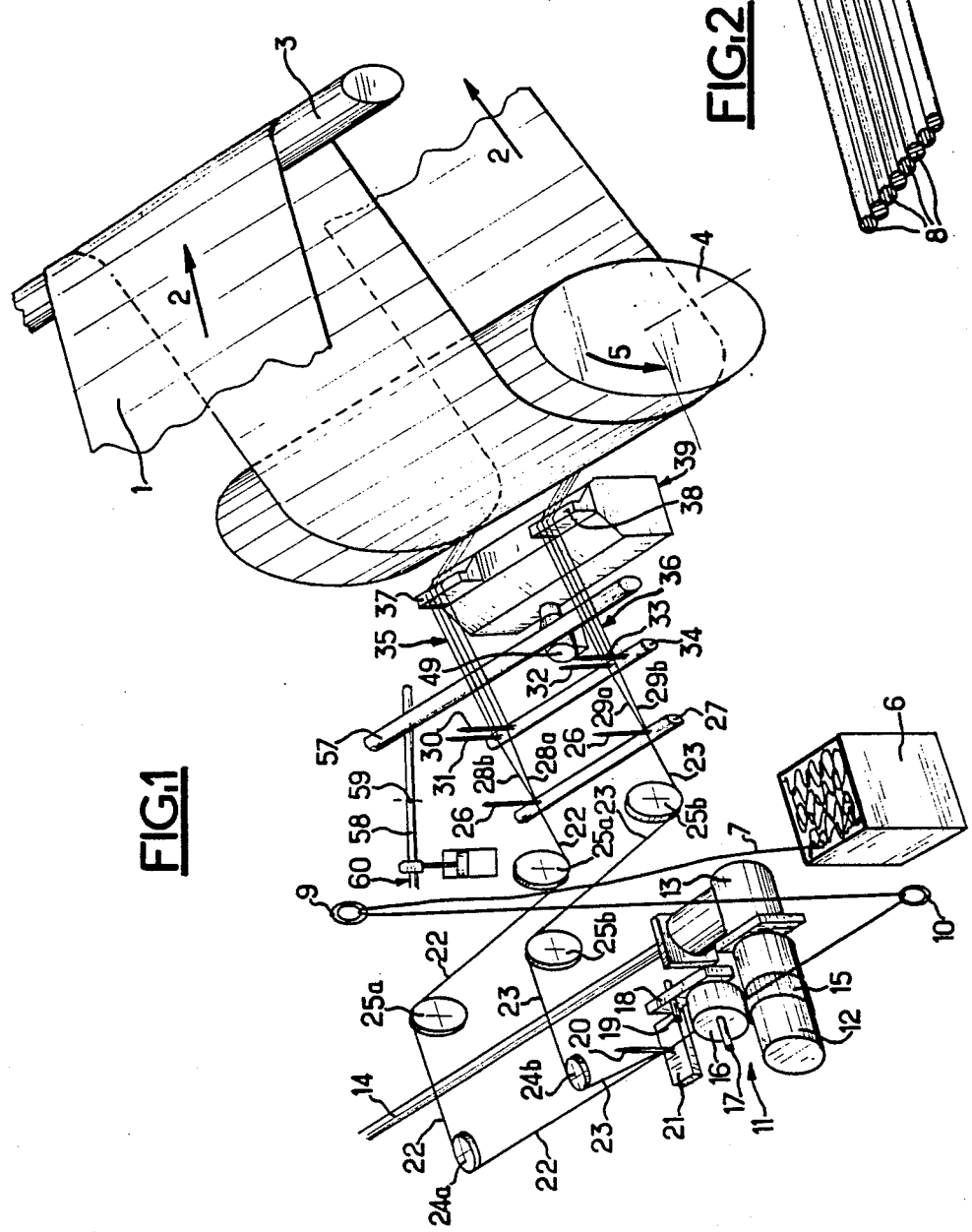

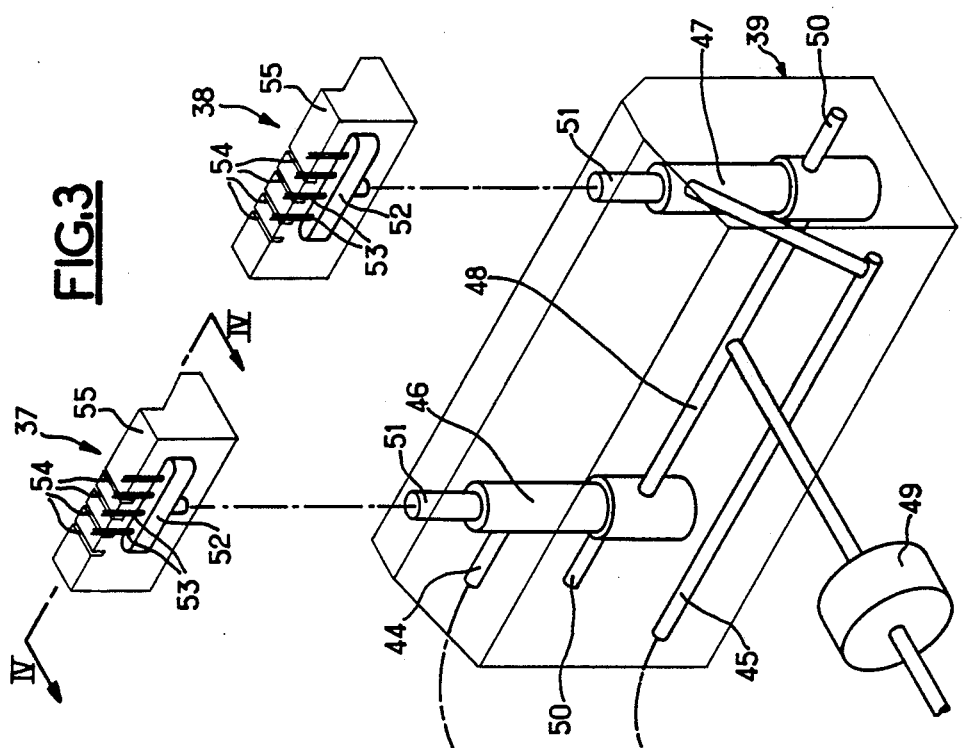
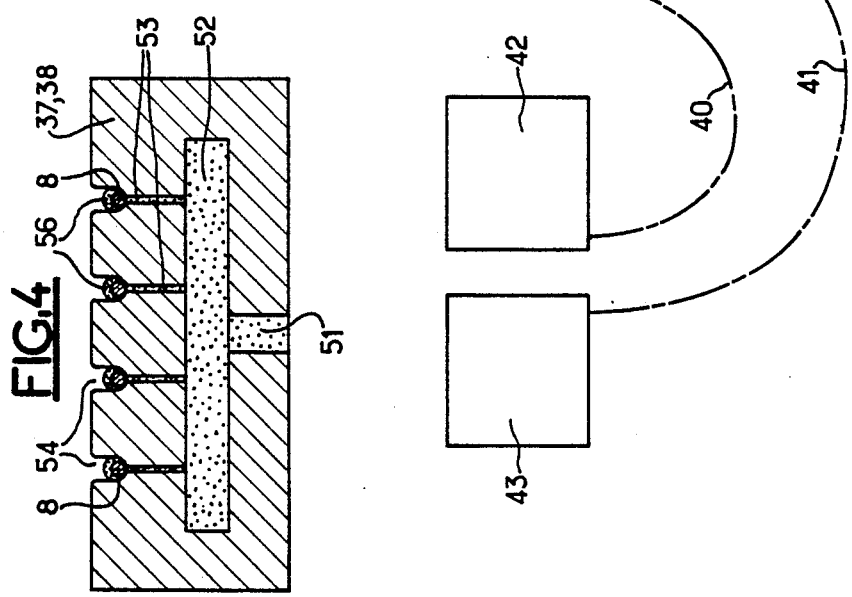

DISPOSABLE DIAPER PANTIE

This application is a continuation of application Ser. No. 910,083, filed Sept. 22, 1986, now abandoned, which is a division of Ser. No. 572,071, filed Jan. 19, 1984, now U.S. Pat. No. 4,666,542.

The present invention relates to a process for the production of disposable diaper panties and also to the diaper panties produced thereby. It is known that the diaper panties which are generally used for infants, but are also used for incontinent adults, comprise in integrated form, as principal elements, a flexible waterproof outer cover serving as pantie and an absorbent pad fixed inside the waterproof cover and optionally lined with an inner web permeable to moisture. This kind of diaper pantie, which is sometimes called "complete change" makes it possible to replace the traditional absorbent diaper and the waterproof pantie which was used in conjunction with the diaper.

It has already been proposed to dispose elastic elements along the openings permitting the passage of the legs, which were worked in the outer waterproof cover serving as pantie. Examples of such diaper panties provided with elastics at the crotch are described in French Patents No. 1,600,732 and No. 2,063,794, for example. Mention may also be made of the diaper panties described in American Patents No. 3,860,003 and No. 4,050,462.

The rectilinear elastics are generally fastened to the waterproof cover by adhesive bonding over at least a part of their length. Use is usually made of elastic bands which are fed continuously in the tensioned state while being in addition held flat, that is to say with one of their main substantially horizontal faces parallel to the surface of the flexible waterproof sheet, which is also fed continuously, on which they are to be fixed. A hot melt adhesive material is intermittently deposited on this face of the elastic bands, for example making use of extrusion means comprising one or more liquid adhesive jets, the operation of which may for example be controlled by compressed air under the control of a solenoid valve.

Owing to the fact that diaper panties produced in this manner are intended to be discarded after use, any even slight reduction of production costs and cost of raw materials is highly desirable.

Moreover, it is important that in diaper panties provided with elastic means of this kind near the crotch, the elastic crotch elements should not apply an excessive gripping action and should not give rise to excessive creasing of the material, particularly of the material constituting the absorbent pad, in order to respect the anatomy of the wearer.

The main object of the invention is to reduce considerably the cost of the raw material used for making the elastic crotch means, while facilitating their fastening by adhesive bonding and reducing the tightnesss of the grip applied to the wearer.

Another object of the invention is to improve the aesthetic appearance of the diaper pantie by forming gathering at the crotch.

The process for the continuous production of disposable diaper panties comprising an absorbent pad laid between an outer cover impermeable to moisture and a permeable lining—the assembly being provided with lateral cutouts to permit the passage of the legs and with rectilinear elastic means fixed to the waterproof cover by adhesive bonding over at least a part of their length and disposed on each side of the absorbent pad—consists in continuously feeding the elastic means, intermittently applying adhesive to them and bring them into contact with the inside face of the waterproof outer cover, which in turn is driven by a rotating drum having a smooth surface.

According to the present invention, the elastic means used comprise a multistrand elastic tape formed by the hot extrusion of individual strands of rubber and by subsequently joining the strands together in a single plane by mutual contact before cooling. A multistrand elastic tape of this kind is therefore fed continuously with a predetermined tension, and is then separated into the various individual strands of which it is composed by passing it on each side of a plurality of successive separators disposed at right angles to the path of the tape.

The original multistrand tape is thus separated into a multiplicity of individual strands, each of a diameter equal to the thickness of the original multistrand tape. The use of a natural latex extruded into bare rubber filaments for the production of a multistrand elastic tape of this kind makes it possible to obtain individual strands of very great elasticity which can withstand elongation ranging up to 300%. It is therefore possible to feed the multistrand elastic tape in such a manner that the tension of each of the individual strands entails maximum elongation at the moment of fastening by adhesive bonding, thus substantially reducing the total amount of elastic material used.

After the separation of each individual strand, each of the strands thus obtained is passed into a longitudinal groove in a hot melt liquid adhesive applicator device, this groove being intermittently fed with liquid adhesive in such a manner that the individual strand passing through the longitudinal groove is immersed over its entire periphery in the liquid adhesive. Passage into the adhesive applicator device therefore makes it possible to obtain for each of the individual elastic strands a tensioned elastic filament completely enclosed in hot melt liquid adhesive at high temperature.

Each of the strands thus intermittently coated with adhesive and held under suitable tension is then continuously brought into contact with the thin sheet intended to serve as waterproof cover for the diaper pantie, this sheet moving over the periphery of a rotating drum having a smooth surface. Taking into account the slight thickness of this sheet and the mass of the rotating drum, the periphery of this drum is at a relatively low temperature in relation to the temperature of the liquid adhesive. It is moreover possible to control this temperature, for example by providing means for the cooling of the periphery of the drum if this should be found necessary. In this way the adhesive material at high temperature coating each of the individual strands before it comes into contact with the waterproof sheet undergoes abrupt cooling as soon as it comes into contact with the waterproof sheet, thus entailing immediate bonding.

The temperature of the rotating drum can easily be selected by the technician with due regard for the parameters comprising the mass of the drum, the mass of the adhesive per unit of length for each of the elastic strands, the temperature of the adhesive immediately before contact, and the nature of the adhesive. In this respect it is appropriate for the difference in temperature between the adhesive which is deposited in the liquid state and the outside surface of the rotating drum to be sufficient to entail an almost immediate bonding action suitable for withstanding the forces to which the elastic strand will be subjected as soon as it is fastened on the cover. In practice it is found that a temperature difference of at least 20° C. is necessary, ad preferably one of 70° to 130°.

In a preferred embodiment of the invention the multistrand elastic tape is first divided into two side tapes through the passing of each of the two side tapes on each side of a preseparator disposed at right angles to the path of the tape. The path of each side tape is then oriented parallel to the movement of the thin sheet intended to form the outer cover of the diaper pantie, the distance between the two side tapes being adapted to the desired distance for the fastening of the elastic means near the crotch on each side of the absorbent pad of the future diaper pantie.

The tension desired for the individual elastic strands is obtained by feeding the multistrand elastic tape by means of a rotary feed roller driven by cooperation with a friction roller coming into contact with the feed roller, preferably through the action of its own weight. In this way it is possible to drive the rotary feed roller in such a manner that the speed of linear displacement of the multistrand elastic tape is lower than the speed of linear displacement of the waterproof sheet serving as cover, which is driven by the rotating drum, the difference in speed giving rise to the tension desired for the elastics.

The multistrand tape can advantageously be fed transversely in relation to the movement of the cover, direction change means then being provided in such a manner that the individual strands arrive parallel to the displacement of the cover at the moment when they come into contact with the cover.

In order to overcome the main difficulty of the process of the invention, namely correct application of adhesive to the different individual strands, provision is made to use one adhesive application unit for each array of individual strands coming from a side tape. Each adhesive application unit comprises a set of longitudinal grooves parallel to one another, which are preferably horizontal and are adapted to each array of individual strands. The adhesive application units are disposed in such a manner that the strands in the tensioned state pass above the said unit, each time passing through the grooves filled intermittently with liquid adhesive.

Each adhesive application unit comprises an adhesive distribution chamber connected by individual passages to each of the longitudinal grooves.

The adhesive applicator preferably comprises two adhesive distributors cooperating with each of the adhesive application units, the supplying of adhesive being controlled by a compressed air circuit provided with a solenoid valve capable of opening and closing the compressed air supply intermittently.

In the process of the invention the absorbent pad and the permeable lining are fastened in a per se traditional manner, by disposing on the waterproof sheet a plurality of parallel longitudinal lines of adhesive distributed over the entire inside surface of the waterproof sheet, these lines of adhesive being formed by extrusion of hot melt adhesive. According to the process of the invention the individual elastic strands are fixed by adhesive bonding, as just stated, between these longitudinal lines of adhesive, in such a manner as to be enclosed, as if inside numerous sheaths, between the waterproof sheet and the other elements of the diaper pantie. In these circumstances, during the transverse cutting-out stage intended to form the diaper panties from a continuous band to which the different elements of the diaper pantie, particularly the absorbent pad, have been applied in succession, the ends of the elastic strands not coated with adhesive spring back inside these sheaths, while on the other hand the parts coated with adhesive which are situated near the crotch give rise to retraction in this zone of the entire diaper pantie, so that numerous pleats or gathers are formed, which prevent any leakage at this point.

According to the invention, the various individual elastic strands are disposed in such a manner that the strand situated closest to the longitudinal axis of the diaper pantie will be very close to the lateral longitudinal edge of the absorbent pad, or may even coincide with this lateral edge. In these circumstances this elastic strand will apply its traction action to a zone of the diaper pantie which, because of the nearness of the absorbent pad, possesses greater strength than the more distant lateral zones subject to the action of the other individual elastic strands, particularly that of those situated farthest from the axis of the diaper pantie.

This differentiated action entails the formation of progressive convexity of the diaper pantie in the outward direction, thus forming a trough perfectly matching the morphology of the wearer.

Moreover, the fact that at each leg opening use is made of a plurality of individual elastic strands disposed parallel permits better distribution over the thigh of the pressure resulting from the traction applied by the elastic means.

Another object of the present invention is the disposable diaper pantie obtained by application of the process of the invention. A disposable diaper pantie of this kind therefore comprises an absorbent pad laid between an outer cover impermeable to moisture and a permeable lining, the assembly having lateral cut-outs to permit the passage of the legs and also having rectilinear elastic means fastened to the waterproof cover by adhesive bonding over at least a part of their length and disposed on each side of the absorbent pad. On each side of the absorbent pad the elastic means comprise an array of at least two individual elastic strands spaced transversely apart, the strand nearest the pad being situated in the immediate proximity of the lateral edge of the pad.

In a preferred embodiment of the invention, the diaper pantie comprises four individual elastic strands on each side of the absorbent pad, the different elastic strands preferably being spaced 4 to 6 mm apart.

The invention will be better understood on examination of one particular embodiment, which is described by way of entirely non-limitative example and illustrated by the accompanying drawings, in which:

FIG. 1 is a schematic view in perspective of a part of an installation permitting the carrying-out of the process of the invention;

FIG. 2 is a partial view in perspective, to a larger scale, of an end portion of a multistrand elastic tape used in the process of the invention;

FIG. 3 is a partially exploded schematic view to a larger scale of the adhesive applicator device used in the installation shown in FIG. 1;

FIG. 4 is a view in section on the line IV—IV in FIG. 3 of one of the adhesion application units of the applicator device shown in FIG. 3;

Figure 5:
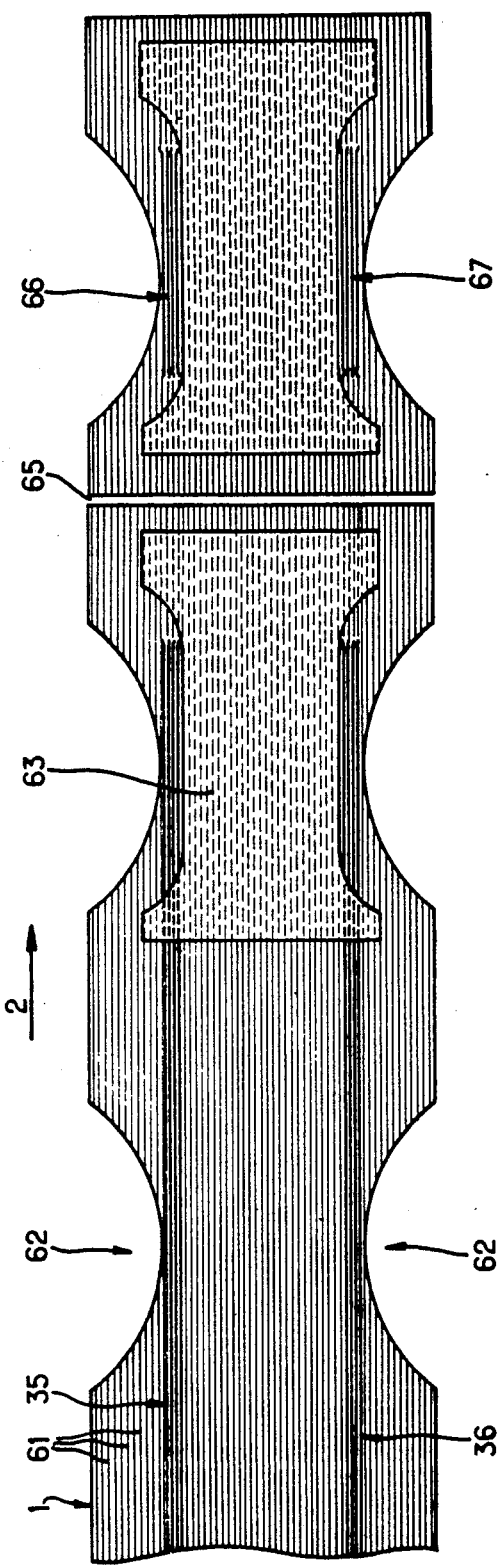
FIG. 5 illustrates a succession of stages in the continuous process of production of the diaper panties according to the invention; F

As can be seen in FIG. 1, a thin waterproof sheet 1 is continuously unwound in the direction of the arrows 2 between a set of rollers, of which one, designated 3, is visible in the Figure, and a rotating drum 4, on the peripheral surface of which the sheet 1 is held in contact along a path corresponding substantially to half the circumference of the drum 4.

The flexible thin sheet 1 is composed of a heat sealable material impermeable to moisture, such as polyethylene. The drum 4 is driven rotationally in the direction of the arrow 5, and its outer surface is kept at a relatively low temperature between 30° C. and 100° C. This temperature can be maintained by forced artificial cooling inside the drum 4 or simply, as illustrated in FIG. 1, through the use of a metal drum of sufficient mass.

On the side of the machine is placed a receptacle 6, inside which is disposed, loosely packed, a multistrand elastic tape 7, of which an enlarged portion can be seen in FIG. 2. It will be noted that inside the receptacle 6 the elastic tape 7 was previously arranged in successive folds of slight length, superposed in likewise successive planes, in such a manner that when the free end of the tape 7 is pulled, it is possible to extract the entire tape contained in the receptacle 6 without the risk of forming knots or tangles which would hinder the feeding of the tape.

Figure 7:
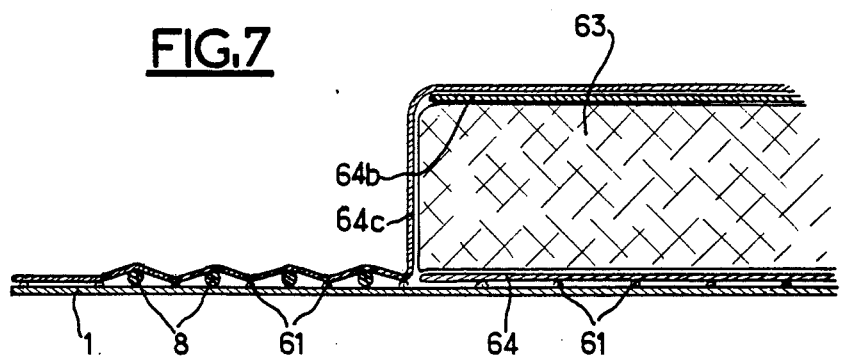
FIG. 7 is a view in cross-section on the line VII—VII in FIG. 6, taken in the crotch zone.

As can be seen in the enlarged view in FIG. 2, the multistrand tape 7 is composed in the example illustrated of the association of eight individual strands 8. A multistrand tape of this kind is produced by individual extrusion of each strand 8, composed of natural latex and extruded in the form of a bare rubber filament. On leaving the extruder, the individual strands are brought into contact in the hot state, and they are joined together by simple fusion along a generatrix, so as to form a substantially plane tape, as can be seen in FIG. 7.

The multistrand tape 7 coming from the receptacle 6 first passes through a first guide ring 9 disposed substantially above the receptacle 6 and the entire machine. The tape 7 then passes downwards to a second guide ring 10 before being introduced into the actual feeding apparatus, given the general reference 11. The path of the multistrand tape 7 between the receptacle 6 on the one hand and the two guide rings 9 and 10 on the other hand makes it possible to extract the tape 7 regularly without applying any considerable tension to it. Any loops which might be formed when the tape leaves the receptacle 6 are eliminated in the course of its movement to the first guide ring 9 or when it passes through the latter.

The feeding apparatus 11 comprises a rotary feed roller 12 driven rotationally by means of a bevel gear set 13 connected by the shaft 14 to the general drive of the machine. On a part of its surface the drive roller 12 is provided with grooves 15, which increase its roughness. A friction roller 16, free to turn on its shaft 17, is supported by a lever 18 able to pivot about a fixed pin 19. This assembly is disposed slightly above and to the side of the feed roller 12 so that the roller 16 comes to bear through its own weight against the grooved portion 15 of the roller 12. The multistrand elastic tape 7 is gripped between the grooved portion 15 of the rotary driven roller 12 and the friction roller 16. In this way the multistrand tape 7 is braked in its linear movement relative to its end bonded to the flexible sheet 1. On the other hand the rotation of the roller 12 applies sufficient traction to the tape 7 to extract it from the receptacle 6. It will be understood that it is sufficient to adjust suitably the speed of rotation of the roller 12 to vary the tension of the elastic tape 7 between the outlet of the feeding apparatus 11 and the point of bonding to the sheet 1.

The elastic tape 7 is fed transversely to the longitudinal axis of the machine, as can be seen in FIG. 1, so that the advantage is gained that the size of the different components is reduced and that the assembly of the feeding device 11 associated with the receptacle 6 containing the elastic tape 7 is facilitated.

On its path across the axis of the machine the multistrand tape 7 is brought into contact with a preseparation rod 20, which is mounted on a fixed base 21 and is disposed vertically, that is to say at right angles to the path of the elastic tape 7. The rod 20 may consist of a simple cylindrical rod having a diameter between 1 and 5 times the diameter of each of the individual strands 8 of the multistrand tape 7. The rod 20 may be replaced by a blade or any other equivalent member situated on the path of the tape 7.

Downstream of the preseparation rod 20 the elastic tape 7 is divided into two lateral tapes 22 and 23, each of which comprises four strands 8 and continues on a horizontal path as far as two guide rollers 24a, 24b disposed equidistantly from the longitudinal axis of the machine, this spacing corresponding substantially to the spacing of the elastic means of the diaper pantie which it is desired to obtain.

The lateral tapes 22 and 23 are then moved while remaining in the same vertical plane, passing over a set of two pairs of rollers 25a and 25b, which bring them into a horizontal plane lower than the horizontal plane in which the feeding was effected and corresponding substantially to the horizontal level of the adhesive application point.

The rollers 24a and 24b have therefore permitted the orientation of each lateral tape 22,23 substantially parallel to the movement of the sheet 1 and with the desired spacing relative to one another. As it passes out of the last two rollers 25a and 25b, each lateral ribbon 22, 23 is further separated by means of separation rods 26 mounted on a fixed cross-member 27. The rods 26 are identical to the preseparation rod 20 and, like the latter, are disposed vertically, that is to say perpendicularly to the movement of the respective lateral tapes 22, 23. They may be in the form of a simple cylindrical rod of the same diameter as the rod 20.

Downstream of the rods 26 the elastic tape is therefore separated on each side of the axis of the machine into two groups of two elastic tapes 28a, 28b and 29a, 29b, each of which is composed of two individual strands 8, which are still joined together.

Each of these elastic tapes 28a, 28b; 29a, 29b is once again separated by passing over a separation rod 30, 31, 32, 33, the four rods being mounted on a fixed cross-member 34.

The four separation rods 30 to 33 are disposed in pairs on the cross-member 34, the rods of each of the pairs, such as 30 and 31 on the one hand and 32 and 33 on the other hand, being disposed a determined distance from one another such that downstream of the separation rods 30 to 33 the elastic tape is converted into two arrays 35,36 of four individual strands 8 lying at a constant distance from one another.

The two arrays 35, 36 of individual strands then pass over respective adhesive application units 37, 38 forming part of an adhesive applicator device 39. The two arrays 35, 36 of strands pass above each adhesive application unit, where they receive the adhesive, as will be explained later on, and then continue on their path while being directed slightly downwards, as can be seen in FIG. 1, until they come into contact with the outside surface of the flexible sheet 1 wound over the periphery of the rotating drum 4.

As soon as it comes into contact with the sheet 1, the liquid adhesive carried by each individual strand 8 of the two arrays 35, 36 is almost instantaneously solidified because of the difference in temperature between the liquid adhesive deposited in the hot state by the adhesive application units 37, 38 and the sheet 1, which is substantially at the same temperature as the periphery of the rotating drum 4, which is kept at a relatively low temperature either by internal circulation of cooling liquid or simply through the size of its metal mass. This being the case, as soon as they come into contact with the sheet 1, which is moving at high speed in the direction of the arrows 2, the eight strands 8, grouped laterally into groups of four in the two arrays 35 and 36, are bonded in the tensioned state to the sheet 1. A difference of linear speed between the sheet 1 and the feeding of the multistrand elastic tape 7 by the feeding apparatus 11 provides the tension desired for the strands 8 thus fixed on the sheet 1.

Referring to FIGS. 3 and 4, it can be seen that the adhesive applicator device 39, containing heating resistors (not shown in the drawings) and carrying the two adhesive application units 37,38 is supplied with liquid adhesive at high temperature by means of the pipes 40 and 41 connected respectively to the tanks 42 and 43, which are provided with means enabling the hot melt liquid adhesive to be kept at a suitable temperature. It will be noted that the usual temperature of an adhesive of this kind is of the order of 150° C. when it passes out of the tanks 42 and 43. The flexible pipes 40 and 41 are connected to internal passages 44, 45 in the adhesive applicator device 39, which lead respectively to two extrusion members 46,47, which are controlled by compressed air coming from the passages 48 and fed with the aid of a solenoid control valve 49, the compressed air being exhausted through the pipes 50 leading outside the applicator device 39.

Each extrusion member 46, 47 is in communication through the passage 51 with an adhesive distribution chamber 52 formed inside each of the adhesive application units 37, 38. The liquid thus extruded into each of the distribution chambers 52 can be extracted therefrom intermittently through the calibrated passages 53 which, in the example illustrated, are four in number, each of them discharging vertically at the bottom of a horizontal longitudinal groove 54 formed in the upper face 55 of each adhesive application unit 37, 38 over its entire width.

The adhesive in the liquid state which is contained in the distribution chamber 52 can feed each of the grooves 54 intermittently when the control solenoid valve 49 is opened, allowing the passage of the compressed air which is capable of driving the liquid adhesive upwards, operating the two two-way distributors (not shown in the drawings) which are situated in each extrusion member 46, 47 and which bring the internal passages 44, 45 into communication with the outlet passages 51. In this position of the solenoid valve 49, liquid adhesive 56 thus fills the bottom part of each of the longitudinal grooves 54. This being the case, each elastic strand 8 passing inside one of these longitudinal grooves 54 is completely immersed in the liquid adhesive, as can be seen in the section in FIG. 4. On leaving each adhesive application unit 37, 38, each strand 8 is thus completely coated with liquid adhesive at high temperature. On leaving the adhesive application units the temperature of the adhesive is of the order of 120° C. As soon as it comes into contact with the flexible sheet 1, the temperature is lowered to below 100°, so that the liquid adhesive is solidified and the strands 8 are bonded to the surface of the sheet 1.

The adhesive application units 37, 38 and the rotating drum 4 are disposed in such a manner that the point of contact of the tensioned elastic strands 8 coated with adhesive is situated below the level of the longitudinal grooves 54 in the adhesive application units 37, 38. In addition, the point of contact of the strands 8 with the sheet 1 is situated substantially half-way along the travel of the sheet 1 in contact with the drum 4.

It will in addition be noted in FIG. 1 that a lifting crossbar 57 is disposed under the two arrays 35, 36 of elastic strands, just upstream of the adhesive applicator device 39. The crossbar 57 can be lifted through the action of the control lever 58, which is pivoted about the pin 59 and the movement of which is controlled by the jack 60. When the entire machine is stationary, it is therefore possible to lift the two arrays of elastic strands 35, 36 in such a manner that they pass out of the longitudinal grooves 54, thus preventing them from being held in contact with the adhesive. Before the machine is restarted, the bar 57 is lowered again and the two arrays 35,36 of four elastic strands resume their position inside the longitudinal grooves 54, as illustrated in FIGS. 1, 3 and 4.

Referring to FIG. 5, it is possible to follow the course of some of the principal stages in the process of producing diaper panties according to the invention. In FIG. 5 the waterproof flexible sheet 1, which moves in the direction of the arrow 2, can be seen once again. In the stage situated furthest to the left in FIG. 5, it can be seen that the sheet 1 has already received the two arrays 35, 36 of elastic strands, which have been bonded over certain parts of their length to the surface of the sheet 1. This sheet has also received, on its own surface, a plurality of parallel longitudinal lines 61 of adhesive, distributed over its entire surface. The strands 8 are fixed between two parallel adhesive lines 61.

After this first stage a cutting operation follows for the purpose of forming leg openings 62, the cutting being continued to a point close to the elastic strand 8 nearest to the outer lateral edge, but without cutting this elastic strand.

Continuing the movement towards the right in FIG. 5, over the surface of the sheet 1 provided with lines of adhesive 61 there is then placed an absorbent pad 63, which may optionally be enclosed between two sheets of permeable cellulose wadding 64a and 64b and then covered with a permeable web of nonwoven material 64c, which can be seen in the sectional view in FIG. 7. These different elements are fastened to the surface of the sheet 1 by means of the longitudinal lines 61 of adhesive.

The resulting continuous band is then cut up transversely to form the various diaper panties. During this operation, comprising cutting along the line 65, the two arrays 35,36 of elastic strands are cut through and therefore spring back to the point where they are bonded to the surface of the sheet 1, thus forming two elastic zones 66, 67 near the crotch of the diaper pantie. It will be noted that this retraction will take place for each elastic strand inside a sheath formed by the surface of the sheet 1 and the permeable web 64c covering it and fixed to it by the parallel lines of adhesive 61. As a simplification, the cut-off diaper pantie shown on the right in FIG. 5 is shown in the tensioned state and without the adhesive fasteners permitting its use.

Figure 6:
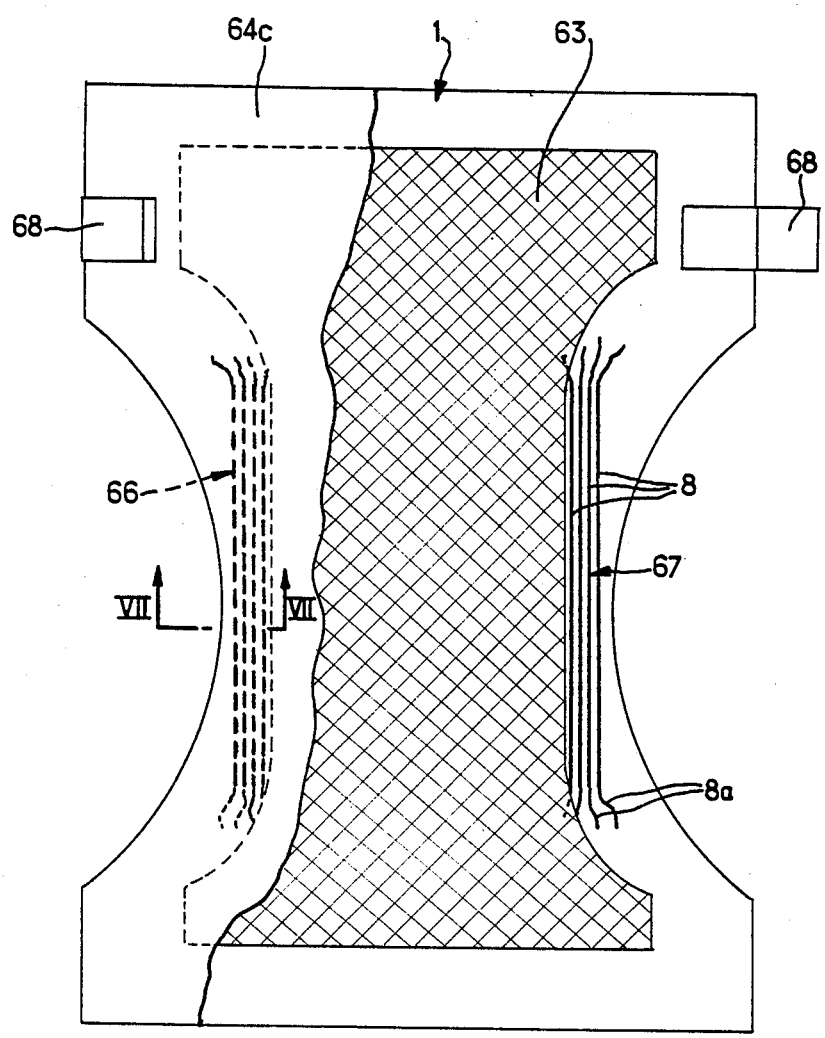
FIG. 6 is a top view, partly broken away, of a diaper pantie according to the invention, in the stretched-out state.
Figure 8:
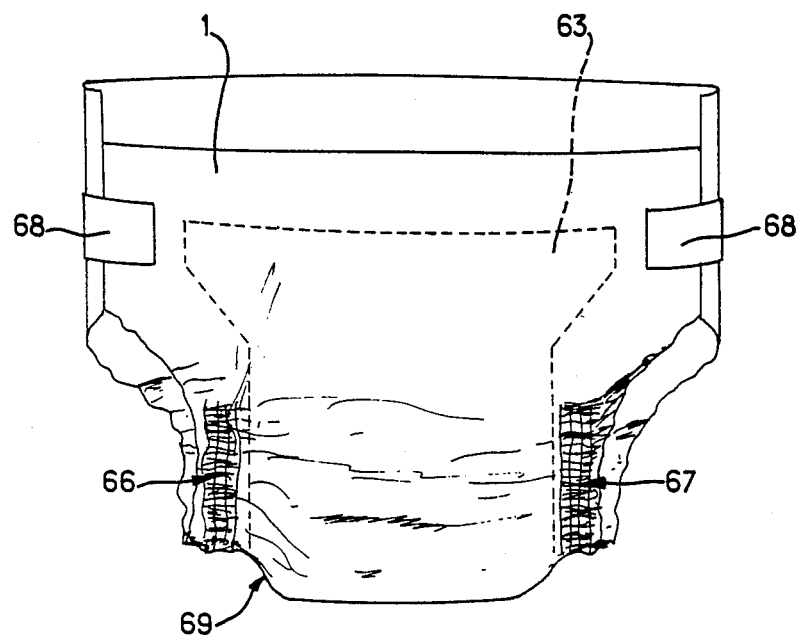
FIG. 8 is an external view of a diaper pantie according to the invention, shown closed and showing the trough shape obtained.

FIGS. 6 to 8 show a diaper pantie produced by the process of the invention. In these diagrammatical Figures can be seen once again the waterproof sheet 1 forming the pantie and the two arrays of elastics 66,67, each composed of four parallel strands bonded to the surface of the sheet 1 parallel to the longitudinal axis of the diaper pantie, close to the crotch zones. The absorbent pad 63 and the upper permeable lining 64c covering the whole arrangement can also be seen again. In FIG. 6 can also be seen the retracted ends 8a, not coated with adhesive, of each elastic strand 8. It will be noted that these ends are of slight length, because of the very great elongation capacity, of the order of 300%, of the elastic strands 8 used.

The rear part of the diaper pantie is also provided with two adhesive fastener devices 68, which are not shown in FIG. 5.

As illustrated in FIG. 6, that is to say in the stretched position of the diaper pantie, it can be seen that the elastic strand 8 of each of the arrays 67, 66 which is situated closest to the absorbent pad 63 is in the immediate proximity of the lateral edge of the pad. The greater rigidity of the diaper pantie at the part where the absorbent pad 63 is situated, and in particular at each of these lateral edges, gives rise to reduced deformability of the diaper pantie in the case of the elastic strand 8 which is situated the closest to the side edge of the absorbent pad 63. On the other hand, the greater the distance from the side edge of the absorbent pad 63, the more flexible the material of the diaper pantie will be and the greater will be the effect of the retraction of the elastic strand. The combination of multiple elastic strands 8 spaced apart from one another and the absorbent pad therefore entails through this action the formation of a trough or outwardly convex surface.

The two arrays 66 and 67 of elastic strands at the crotch will, when left to themselves, apply traction to the material of the diaper pantie which, in the proximity of the crotch, where there is progressive outwardly directed convexity as seen in FIG. 8, will assume the shape of a trough 69, which permits better fitting on the infant or user. On each side of the absorbent pad 63, in the proximity of the crotch, there are disposed four parallel elastic strands, each spaced 4 to 6 mm from the adjacent strand. This arrangement is seen again in the sectional view shown in FIG. 7. The pressure due to the elastic grip on the thighs is better distributed, because it is divided among a plurality of strands 8. Finally, the external appearance of the diaper pantie is improved by the formation of a gathered edge on each side of the absorbent pad in the crotch zone, as can be seen in FIG. 8.

I claim:
1. A disposable diaper, comprising:
    an absorbent pad located between an impervious backing sheet and a permeable inner liner sheet,
    a plurality of longitudinal coatings of adhesive material distributed over at least side marginal portions of the inside face of said backing sheet and extending over its entire length,
    both said backing sheet and said liner being provided with lateral cutouts enabling the passage of the legs, and the delineation of a crotch zone,
    said absorbent pad being smaller in width than said backing sheet and said inner liner, at least in said crotch zone, so that said side marginal portions extend outwardly beyond the side edges of said absorbent pad,
    the inside face of said backing sheet being provided with two arrays, each of at least two rectilinear individual elastic strands positioned parallel to each other, said arrays being unconnected to each other and spaced transversely apart from one another, said strands of each array being provided on each side of said side marginal portions of said backing sheet,
    said strands of each array being located in channels between two of said longitudinal coatings of adhesive,
    each said individual elastic strand being affixed in stretched condition to said inside face of said backing sheet in the crotch zone of the diaper by an adhesive material coated on said elastic strand, both end portions of each individual strand being free from adhesive material and from transverse joining members and being unaffixed to said backing sheet, and said liner in said channels,
    so that said end portions are retracted in said channels within the diaper, between two of said longitudinal coatings of adhesive,
    the elastic strands which are situated closest to the absorbent pad being positioned close to the lateral edge of the pad so that both arrays of elastic strands act upon the lateral edges of the pad to form the crotch zone of the diaper into a trough-like shape of outwardly convex surface, providing differentiated traction forces, due to each individual elastic strand.
2. Diaper pantie according to claim 1, wherein the elastic strands are at least four in number on each side of the absorbent pad.
3. Diaper pantie according to claim 1, wherein the individual elastic strands are spaced 4 to 10 mm, preferably about 6 mm, apart.

* * * * *